United States Patent [19]
Rose et al.

[11] Patent Number: 6,008,283
[45] Date of Patent: Dec. 28, 1999

[54] OLIGOMERIC FLAME RETARDANT ADDITIVE

[75] Inventors: Richard S. Rose; Gurudas Zingde; David M. Hemmerly, all of West Lafayette, Ind.

[73] Assignee: Great Lakes Chemical Corporation, West Lafayette, Ind.

[21] Appl. No.: 09/044,286

[22] Filed: Mar. 19, 1998

Related U.S. Application Data

[60] Provisional application No. 60/039,372, Mar. 20, 1997.

[51] Int. Cl.$^6$ .............................. C08K 5/03; C07C 25/18; C07C 25/22
[52] U.S. Cl. .......................... 524/411; 524/467; 524/469; 570/182; 570/183; 570/184
[58] Field of Search ...................................... 524/412, 467, 524/469; 526/280, 293; 570/183, 184, 182

[56] References Cited

U.S. PATENT DOCUMENTS

| | | |
|---|---|---|
| 2,243,543 | 5/1941 | ter Horst . |
| 2,757,146 | 7/1956 | Fawcett . |
| 2,914,489 | 11/1959 | Hall . |
| 2,954,412 | 9/1960 | Wulf et al. . |
| 3,221,068 | 11/1965 | Gorham . |
| 3,943,195 | 3/1976 | Naarmann et al. . |
| 4,753,745 | 6/1988 | Kostusyk et al. ....................... 570/183 |
| 5,302,768 | 4/1994 | Hussain . |

FOREIGN PATENT DOCUMENTS

| | | |
|---|---|---|
| 2 050 009 | 5/1971 | Germany . |
| 27 58 781 | 7/1979 | Germany . |
| 1270318 | 4/1972 | United Kingdom . |

OTHER PUBLICATIONS

Chemical Abstracts Service, Registry No. 71297–41–1.
Chemical Abstracts Service, Registry No. 71329–92–5.

*Primary Examiner*—Veronica P. Hoke
*Attorney, Agent, or Firm*—Woodard, Emhardt, Naughton, Moriarty & McNett

[57] ABSTRACT

Flame retardants comprising oligomeric bromine-containing compounds comprising aryl groups that are connected by aliphatic chains are described. Flame retardant compositions comprising the flame retardants of the present invention and flame retardant aids are also described. Polymeric compositions comprising the flame retardants of the present invention optionally combined with a flame retardant aid, along with a method of fireproofing a material, are further described.

15 Claims, No Drawings

6,008,283

OLIGOMERIC FLAME RETARDANT ADDITIVE

This application claims the benefit of U.S. Provisional Application No. 60/039,372 filed Mar. 20, 1997.

FIELD OF THE INVENTION

The present invention relates generally to oligomeric flame retardants, and more particularly to oligomeric bromine-containing compounds having a high bromine content connected by short aliphatic chains.

BACKGROUND OF THE INVENTION

Compounds containing high levels of aromatically-bound bromine have been used extensively for many years. An excellent example is decabromodiphenyl oxide. This compound is characterized by efficiency as a flame retardant additive anid good thermal stability.

More recently, oligomeric flame retardant additives have been used in commercial polymers. These compounds also contain aromatically-bound bromine. They melt at lower temperatures than the type of compound cited above and blend readily with many thermoplastic resins. A benefit of the oligomeric flame retardants is the improved melt flow of thermoplastic resins containing them.

Another advantage of these higher molecular weight flame retardants is their resistance to migration when incorporated into a polymer matrix. Migration is observed as a powdery deposit on the surface of the polymer or on the surface of a mold.

Further, it has been shown that higher molecular weight compounds, such as oligomers, tend to be less soluble, and therefore less toxic, than smaller, lower molecular weight compounds.

Each type of oligomeric flame retardant introduced thus far has inherent disadvantages. For example, uncapped brominated epoxy oligomers exhibit black specks that are formed during compounding and decreased melt flow due to chemical interaction. Even when capped, the epoxy oligomers still possess potentially reactive hydroxyl groups.

Carbonate oligomers also need to be capped. They tend to be unstable during compounding. Moreover, acrylate oligomers are prone to depolymerization under heat and shear. Furthermore, their ester linkages can also hydrolyze over time.

The lower bromine content of current oligomeric flame retardants reduces their efficiency. The higher loading requirements to achieve the desired flammablility test performance often result in decreased physical properties.

Moreover, concern exists that some of these compounds (such as brominated diphenyl oxides) may be hazardous to human health. It has been suggested that compounds having oxygen atoms attached to aromatic rings may be altered under certain thermal and atmospheric conditions to yield toxic dioxins and dibenzofurans.

In designing new chemical structures, it may be deemed advantageous to avoid oxygenated aromatic species. A more recently introduced flame retardant, decabromodiphenyl ethane (U.S. Pat. No. 5,302,768), has a high bromine content and no oxygen on the aromatic rings. However, its high melt range and tendency to migrate, particularly in olefinic resins, are drawbacks.

There is still a need for a flame retardant additive that contains no aromatic oxygen, is thermally stable, exhibits lack of bloom, good melt flow of the oligomers and has a high bromine content.

SUMMARY OF THE INVENTION

Briefly describing one aspect of the present invention, there are provided oligomeric flame retardants comprising ring-brominated aryl groups connected by aliphatic chains. The aliphatic chains may be branched or linear, and any aryl groups that are not single, six-carbon aromatic rings may be further substituted with branched or linear alkyl groups.

Another aspect of the present invention provides flame retardant compositions comprising oligomeric bromine-containing compounds comprising ring-brominated aryl groups connected by aliphatic chains and a flame retardant aid. The flame retardant aid may be a synergist, such as antimony-containing compounds like antimony oxide.

Another aspect of the present invention provides polymeric compositions comprising a polymer and a flame retardant, wherein the flame retardant comprises an oligomeric bromine-containing compound comprised of aryl groups that are connected by aliphatic chains. For aryl groups comprised of other than a single six carbon aromatic ring, the aryl group may be further substituted with branched or linear alkyl groups. The polymer typically includes thermoplastic resins, thermoset resins, coatings, or adhesives. The flame retardant may further include a flame retardant aid, which may be a synergist.

Another aspect of the present invention provides a method of fireproofing a material by contacting the material with a flame retardant comprising an oligomeric bromine-containing compound comprised of aryl groups that are connected by aliphatic chains is also provided. The flame retardant may include a flame retardant aid.

One object of the present invention is to provide a flame retardant composition comprising oligomeric bromine-containing compounds comprised of aryl groups that are connected by aliphatic chains.

Another object of the present invention is to provide a flame retardant composition comprising oligomeric bromine-containing compounds comprised of aryl groups that are connected by aliphatic chains and a flame retardant aid.

A further object of the present invention is to provide a polymeric composition comprising a polymer and a flame retardant comprising an oligomeric bromine-containing compound comprised of aryl groups that are connected by aliphatic chains and optionally including a flame retardant aid.

A further object of the present invention is to provide a method of fireproofing a material.

Another object of the present invention is to provide a thermally stable flame retardant that exhibits good melt flow of the constituent oligomers and lack of bloom.

DESCRIPTION OF THE PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

The preferred oligomeric bromine-containing compounds of the present invention are indicated by the formula:

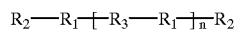

wherein
- n is from 1 to 11;
- $R_1$ is a branched or linear alkylene group;
- $R_2$ is an aryl group having an average of from about 2 to about 5 ring-substituted bromine atoms per aromatic ring; and
- $R_3$ is an aryl group having an average of from about 2 to about 4 ring-substituted bromine atoms per aromatic ring.

$R_1$ contains from 1 to 6 carbon atoms, and preferably contains from 1 to 4 carbon atoms. As used herein, alkyl means a saturated or unsaturated aliphatic hydrocarbon which may be either straight chain or branched and includes methyl, ethyl and structural isomers of propyl, butyl, pentyl and hexyl. When both ends of the alkyl group terminate in a bond to another atom, the group is called an alkylene group and includes methylene, ethylene and structural isomers of propylene, butylene, pentylene and hexylene.

Aryl, as used herein, means a group whose molecules have the ring structure characteristic of, for example, benzene, naphthalene, anthracene and fluorene. For example, an aryl group includes phenyl, naphthyl, anthracyl, phenanthryl, fluorenyl and biphenyl.

Preferred compounds contain repeating units n of from about 1 to about 7. $R_2$ preferably contains an average of from about 3 to about 5 ring-substituted bromine atoms per aromatic ring. $R_3$ preferably contains an average of from about 3 to about 4 ring-substituted bromine atoms per aromatic ring.

Any $R_2$ or $R_3$ that are comprised of something other than a single six carbon aromatic ring are optionally alkylated. For example, where $R_2$ and $R_3$ are comprised of other than a single six carbon aromatic ring, they may be further monosubstituted, disubstituted or multi-substituted with a linear or branched alkyl group. The alkyl group typically contains from 1 to 8 carbon atoms.

Several literature references disclose methods of preparing oligomers relevant to this invention, including U.S. Pat. No. 2,757,146, Sorensen and Campbell, "Preparative Methods of Polymer Chemistry", *Interscience*, 1961, and Winberg, Fawcett, Mochel, and Theobald, *Journal of the American Chemical Society* 82, 1428–35, 1960. These methods include the Friedel-Crafts alkylation of the example below. The descriptions contained in the foregoing references are hereby incorporated by reference.

The compounds of the present invention may be prepared in a number of ways. For example, they may be prepared by reacting molecules which already contain aromatically-bound bromine, or by making oligomers which are then brominated.

Similarly, methods for the bromination of aromatic rings of a compound are well known. For example, U.S. Pat. No. 5,302,768 cited above as well as the following references disclose the bromination, isolation, and purification of brominated diphenyl alkane: WO/9608457, WO/9615087, EP347116, EP489406, and U.S. Pat. Nos. 5,008,477, 5,030,778, 5,124,496, 5,324,874 and 5,401,890. Methods are also known in the art for producing higher molecular weight compounds of the present invention by reacting certain aromatic bromine-containing compounds, including methods disclosed in U.S. Pat. No. 4,567,218, hereby incorporated by reference.

The oligomeric bromine-containing compounds may be incorporated into a polymer to form a polymeric composition. Preferred polymers include thermoplastic resins, thermoset resins, coatings and adhesives. For example, the thermoplastic resins may include homopolymer and copolymer acetals, acrylics, acrylonitrile-butadiene-styrene (ABS), polyamides (e.g., nylons) and polyarylates. The thermoset resins include polyurethanes, polyesters, silicones, polyimides and bismaleimides. Furthermore, the coatings and adhesives include acrylate polymers and styrene-butadiene copolymers.

Polymeric compositions containing flame retardant additives are generally tested to determine the effect of the additive upon flammability and other physical properties. These flammability and physical properties are determined by the end use of the polymer containing the flame retardant additive and can be used by one of skill in the art to assess the amount of the inventive flame retardant to be used for the required level of retardancy. However, the polymeric compositions are typically comprised of from about 5 to about 20 weight percent of flame retardant and further preferably from about 7 to about 15 weight percent of flame retardant.

Methods of incorporating flame retardant additives into a polymer are also well known. Solid or liquid additives are added to thermoplastics before or during extrusion or molding. Flame retardant additives are added to thermosets before or during polymerization.

In one embodiment of the present invention, the flame retardant is combined with a flame retardant aid as is known in the art to form a flame retardant composition. The flame retardant aid includes a synergist. The synergist typically includes an antimony-containing compound, including antimony oxide, antimony pentoxide, sodium antimonate and preferably antimony trioxide. The synergists also include tin-containing compounds such as zinc stannate and boron-containing compounds such as zinc borate. The synergists are typically present in a weight ratio of about one part antimony to 2 to 5 parts halogen. However, when the flame retardant composition includes a boron-containing compound such as zinc borate, thes composition typically contains about 0.1% to about 0.7% by weight of the boron-containing compound for every 1% halogen by weight in the composition. Coflame retardants, including halogen-containing compounds, phosphortus-containing compounds, and nitrogen-containing compounds may also be combined with the oligomeric bromine-containing compounds to form a flame retardant composition. Examples of such phosphorus-containing compounds include inorganic phosphorus compounds such as ammonium phosphates, organic phosphorus compounds such as triphenyl phosphate, triethyl phosphate and alkyl phosphates, and halogenated alkyl phosphates and phosphonates such as tris(2-chloroethyl) phosphate, bis(2-chloroethyl)vinylphosphonate and bis(2-chloroethyl) 2-chloroethylphosphonate. Furthermore, examples of such halogenated compounds include decabromodiphenyl oxide, decabromodiphenyl ethane, tetrabromobisphenol A and hexabromocyclododecane. Examples of such nitrogen-containing compounds include melamine and melamine cyanurate.

In another embodiment of the present invention, a method of fireproofing a material is provided comprising the step of contacting the material with a flame retardant comprising the oligomeric bromine-containing compounds of the present invention above described. The flame retardant may further include a flame retardant aid. The material includes polymers such as thermoset resins, thermoplastic resins, and articles made from such polymers as are known in the art. The quantity of flame retardant that contacts the material will depend on the nature of the material, the degree of fireproofing desired, the shape of the article the material is comprised of and whether other additives are present in the flame retardant that is applied.

Reference will now be made to specific examples using the processes above described. It is to be understood that the examples are provided to more completely describe preferred embodiments and that no limitation to the scope of the invention is intended thereby.

EXAMPLE 1
Preparation of a Higher Brominated Oligomer 351.5 grams of benzene and 12 grams $AlCl_3$ were added to a liter flask equipped with a thermometer, heating mantle, stirrer, and condenser. The mixture was heated to 60° C. with stirring. Over two hours, 222.8 grams 1,2-dichloroethane was added. The reaction mixture was then heated to 104° C. for 2.5 hours and allowed to cool to 20° C.

30 ml water was added to the resulting viscous liquid, raising the temperature to 43° C. A separatory funnel was used to recover the organic layer, yielding 426.1 grams of oily liquid. This liquid was placed under a vacuum of 24 mm mercury and the temperature raised to 150° C. over 1.5 hours. The recovered oligomer, oligo((phenylethyl) benzene), weighed 263.6 grams.

Over 30 minutes, 52.1 grams of oligomer was added to 799 grams bromine to which had been added 1.5 grams of powdered iron. The temperature of the bromine was allowed to rise from 5° C. to 16° C. during the addition.

The product was recovered by first steam distilling at 102° C. A 250 ml volume of water was added to the crude product and stirred for 3 hours at 20° C. The solid product was filtered and dried at 100° C., yielding 212 grams. Analysis of the brominated oligo((phenylethyl)benzene) product showed 81% bromine (the product was perbrominated) and a melt range of 119° C. to 218° C.

EXAMPLE 2
1,4-Dibenzylbenzene

In a 4 neck, 1 liter flask fitted with thermocouple, mechanical stirrer, Barrett trap with condenser, nitrogen line, and stopper, was added 1,4-dibenzoylbenzene (90.5 g), hydrazine monohydrate (172.4 g) and diethyleneglycol (400 ml). The reaction mixture was heated at 100° C. for 1.5 hours. The mixture was then heated to 150° C. while collecting water and excess hydrazine hydrate in the Barrett trap. Potassium hydroxide (54.1 g) was slowly added over 0.5 hour while the temperature was slowly increased to 200° C. The temperature was maintained at 200° C. for 1 hour. The reaction was cooled to 80° C. and then poured into 500 ml water. The reactor was rinsed with an additional 550 ml water and combined with the quench solution. The water was extracted 3 times with 250 ml dichloromethane, the combined organic phases were washed with 500 ml water, dried over magnesium sulfate, filtered and the solvent removed on a rotary evaporator to give 1,4-dibenzylbenzene as a white solid (79.5 g, 97.4% yield).

EXAMPLE 3
Brominated 1,4-Dibenzylbenzene:

The reaction system for the bromination step consisted of a 2 liter, 4 neck round-bottom flask fitted with mechanical stirrer, thermocouple connected to a controller, a solid addition funnel and a condenser connected to a recirculating trap consisting of a teflon gas inlet tube from the reactor oriented above the surface of the water (2 L) in the flask, a packed column filled with glass helices, and a recirculating loop used to pump the trap contents to the top of the column. The trap was filled with 2 L water. Iron powder (4.2 g) was added to bromine (2482 g) at room temperature in the reactor. The recirculating loop in the scrubber was turned on. The reaction solution was stirred for 30 minutes and 1,4-dibenzylbenzene (82.2 g) was added over circa 2 hours via the addition funnel. The reaction mixture was heated to 50° C. over 2 hours and then held there for 5.5 hours. The reactor was allowed to cool to room temperature and 1 L aqueous hydrobromic acid (500 ml 48% hydrobromic acid and 500 ml water) was added. A Barrett trap was placed between the reactor and the condenser. The majority of the excess bromine was removed by distillation. The slurry was filtered and the brominated 1,4-dibenzylbenzene product washed with water and dried overnight at 100° C. to give a light colored solid (352 g, 98% yield, bromine content 79.6% wherein each aromatic ring has, an average of about 4 bromine atom substituents, mp greater than 375° C.).

EXAMPLE 4
1,3-Dibenzylbenzene:

In a 4 neck, 1 liter flask fitted with thermocouple, mechanical stirrer, Barrett trap with condenser, nitrogen line, and stopper, 1,3-dibenzoylbenzene (197 g) and hydrazine monohydrate (280 g) were heated in diethyleneglycol (540 ml) at 100° C. for 4 hours. The mixture was then heated to 160° C. while collecting water and excess hydrazine hydrate in a Barrett trap. Potassium hydroxide (43.7 g) was slowly added over 0.5 hour while the temperature was slowly increased to 200° C. The temperature was maintained at 200° C. for 1 hour. The reaction was cooled to room temperature and 1 L of water was added and stirred for 20 minutes. The contents were transferred to a separatory funnel. The reactor was rinsed with 250 ml dichloromethane and the rinse added to the water layer. The water was extracted three times with dichloromethane (250 ml each) and the combined organic phases were backwashed with 1 L water. The organic phases were dried over magnesium sulfate, filtered and the solvent removed on a rotary evaporator to give 1,3-dibenzylbenzene as a pale yellow liquid (168.3 g, 94.7% yield).

EXAMPLE 5
Brominated 1,3-Dibenzylbenzene:

The reaction system for the bromination step consisted of a 2 liter, 4 neck round-bottom flask fitted with mechanical stirrer, thermocouple connected to a controller, an addition funnel and a condenser to a recirculating trap consisting of a TEFLON® gas inlet tube from the reactor oriented above the surface of the water (2 L) in the flask, a packed column filled with glass helices, and a recirculating loop used to pump the trap contents to the top of the column. The trap was filled, with 2 L water. Iron powder (4.5 g) was added to bromine (2227 g) in the reactor at room temperature. The solution was stirred for 30 minutes and 1,3-dibenzylbenzene (102 g) was added over circa 2 hours. The reaction mixture was heated to 50° C. over 0.5 hour and held there for 6 hours. The reactor was allowed to cool to room temperature and then 423 g 48% hydrobromic acid and 450 ml water was added. The majority of the excess bromine was removed by distillation. The slurry was filtered and the brominated 1,3-dibenzylbenzene product washed with water and dried at 100° C. to give a light colored solid (364 g, 82% yield, bromine content 79.8% wherein each aromatic ring has an average of about 4 bromine atom substituents, mp 334–344° C.).

EXAMPLE 6
Poly((phenylmethyl)benzene):

Benzyl chloride (150 g) was added to a suspension of aluminum chloride (2.16 g) in benzene (176.4 g) to maintain the reaction temperature at about 35° C. The reaction mixture was stirred for 0.5 hour after addition was completed and then poured onto a slurry of hydrochloric acid in ice. The benzene layer was separated and the aqueous phase washed twice with 300 ml dichloromethane. The combined organic phases were washed with sodium bicarbonate solution followed by water. The organic phase was dried over magnesium chloride, filtered and the solvents removed on a rotary evaporator. Diphenylmethane was removed via a bulb-to-bulb distillation at 0.2 torr and 120° C. air temperature. The pot bottoms consisted of the desired oligomers (133.6) and were carried on to the bromination step without further purification.

EXAMPLE 7

Brominated poly((phenylmethyl)benzene):

The reaction system for the bromination step consisted of a 2 liter, 4 neck round-bottom flask fitted with mechanical stirrer, thermocouple connected to a controller, and addition funnel and a condenser connected to a recirculating trap consisting of a TEFLON® gas inlet tube from the reactor oriented above the surface of the water (2 L) in the flask, a packed column filled with glass helices, and a recirculatirg loop used to pump the trap contents to the top of the column. The trap was filled with 2 L water. Iron powder (5.3 g) was added to bromine (2682 g). Oligomer (104.9 g) was added to the reactor over 1 hour. The reaction mixture was heated to 58° C. for 8.5 hours. The reaction mixture was cooled to room temperature and water (500 g) was added. Bromine was removed by distillation and after 700 g had been removed, an additional 500 g of water was added to the reactor and distillation continued. The reactor was cooled to room temperature and the solid collected by filtration. The material was washed with water and dried. The material was then slurried in dichloromethane (600 g) overnight. The solid was collected in a filter, and washed with toluene and dried overnight to give a tan solid product of brominated poly((phenylmethyl)benzene)(350 g) that contained 76.2% bromine (an average of about 3.4 bromine atoms per aromatic ring).

EXAMPLE 8

Flame Retardant Polystyrene Composition

A small Brabender Plasticorder was used to blend 50 grams Huntsman Chemical Corporation 333 (HCC 333) polystyrene resin, 7 grams of the product described in Example 1, 2 grams antimony oxide, 2 grams Stereon 840 A (Firestone) modified rubber, and 0.05 grams octadecyl-3-(3', 5' di t-butyl-4'-hydroxyphenyl) propionate stabilizer.

Processing conditions were ten minutes at 210° C. and 40 rpm. The Example 1 product appeared to melt blend. The compounded plastic was compression molded for four minutes at 350° F. (177° C.) into ⅛ inch (0.32 cm) plaques. Material cut from the plaques met the requirements of the UL-94 flammability test V-0 (best) rating.

EXAMPLE 9

Flame Retardant Coating Composition

The product of Example 1 was ground in a pestle and mortar to eliminate large particles. 36 grams of particles was added slowly to a solution of 24 grams water and 1 gram nonylphenol surfactant (Union Carbide Triton X-301) under agitation provided by a mixer blade. 18 grams antimony oxide was then added slowly, and mixing continued for five minutes. Fifteen drops of 28% ammonium hydroxide solution and 1.0 gram acrylic thickener (Rohm and Haas ASE-60) were added, also under agitation.

The resulting water based dispersion was blended with an acrylic latex coating (Rohm and Haas Rhoplex HA-24) to give a level of flame retardant additive (the product of experiment: 1 and antimony oxide) of ten percent based upon the solids weight of the coating (44.5% by weight).

A 6.5 oz/yd$^2$ (220.4 g/m$^2$) fabric, coated with a weight (after oven drying to remove all water) of 2.7 oz/yd$^2$ (91.5 g/m$^2$) of the polymer blend of the preceding paragraph, was tested by flammability test MVSS-302. It achieved the best rating, SE, with no burn past the first (1.5 inch, 3.8 cm) mark. The same fabric, coated with the same weight of coating which did not contain the flame retardant additives, failed the MVSS-302 test with a burn distance of greater than 10.0 inches (25.4 cm) past the first mark.

EXAMPLE 10

Flame Retardant Unsaturated Polyester Composition

Two laminates were made using a general purpose phthalate. polyester resin. Additives in the first included 14 parts per hundred resin (phr) of the composition by weight of Example 1, 4 phr antimony oxide, 0.5 phr 6% cobalt naphthenate, and 1.0 phr 60% MEK peroxide. The second laminate contained only the peroxide and naphthenate cure promoters at the same phr levels.

The laminates contained 3 plies of 1.5 oz/yd$^2$ (50.9 g/m$^2$) chopped strand glass fiber mat. Total laminate thickness was ⅛ inch (0.32 cm) and the glass content was approximately 30% by weight.

The resin was allowed to cure at ambient temperature, followed by a post-cure of 1 hour at 100° C. Burn test specimens were cut with a water-cooled diamond blade. Both oxygen index (ASTM D-2863) and Hooker Laboratory intermittent flame Test (HLT—a vertical flame test) were conducted.

The oxygen index of the base resin laminate was 19. The oxygen index of the laminate containing the oligomer described in Example 1 was 28. The HLT value for the base resin was 0 (worst possible). The laminate containing the oligomer described in Example 1 had an HLT value of 100 (best possible).

EXAMPLE 11

Flame Retardant Acrylonitrile-Butadiene-Styrene (ABS) Composition

Four ABS resin compounds were prepared. One was comprised of the base resin only (Bayer Lustran 633 ABS) and the second was comprised of, by weight, 76.4% ABS resin, 13.5% of the oligomer described in Example 1, 4.5% of a 90% antimony oxide concentrate, 3.5% chlorinated polyethylene (Dow Tyrin 4211), 2.0% titanium dioxide, and 0.1% stabilizer (Anox PP-18, Great Lakes Chemical Corp.).

Compounds 3 and 4 had the same weight percentages of all components as the second compound except for ABS resin and brominated flame retardant additive. Compound 3 contained, by weight, 73.9% ABS resin and 16.0% of bis(tribromophenoxy) ethane. Compound 4 contained, by weight, 73.9% ABS resin and 16% of an epoxy oligomer based upon tetrabromobisphenol A (Dainippon EC-20).

Compounding was done in a Brabender mixer at 210° C. and 40 rpm for 10 minutes. Test bars were then molded at 410° F. (210° C.). UL-94 flammability test results were V-0 (best rating) for the ABS compound containing the oligomer described in Example 1 and the compound containing bis (tribromophenoxy) ethane (compound 3). The compound containing EC-20 (compound 4) did not meet the V-0 criteria. It had a V-2 rating. The compound containing the base resin only failed the UL-94 flammability test.

EXAMPLE 12

Flame Retardant Polystyrene Composition

The brominated compounds from Examples 3, 5, and 7 were evaluated as flame retardants in high impact polystyrene. Three separate formulations were prepared by dry blending the following components, compounding them in a 25 mm twin screw extruder at temperatures of 200° C.–210° C., and then pelletizing them: HCC 333 polystyrene resin (77.1%), brominated flame retardant (13.2%) (from Examples 3, 5, or 7), antimony trioxzide (3.6%), Stereon 840A rubber (4.0%) (Firestone), titanium dioxide (2.0%), and Anox PP18 Antioxidant (Great Lakes Chemical Corporation) (0.1%) (all percentages being by weight).

The compounded pellets were injection molded into test bars 6 inches (15.2 cm) long by ½ inch (1.3 cm) wide by 1/16 inch (0.16 cm) thick using a Model HI-30RS Newbury Injection Molding Machine. The bars were tested as in Example 8 using the UL-94 flammability standard, and all three formulations were found to have a rating of 94V-2. Bars containing all of the components except for the brominated compounds did not qualify for a UL-94 rating.

EXAMPLE 13

Oligomeric bromine-containing compounds of the present invention wherein n is from 1 to 11, and wherein the alkylene group contains from 1 to 6 carbon atoms function as flame retardants in the present invention. For example, the oligomeric bromine-containing compounds described in the application having n equal to 1, 3, 5, 7, 9, or 11 and wherein the alkylene group is methylene, or structural isomers of propylene (such as isopropylene) or pentylene function as flame retardants.

Furthermore, combination of the oligomeric bromine-containing compounds described in this Example with flame retardant aids or coflame retardants yield useful flame retardant compositions. For example, combining the compounds described in this Example with antimony trioxide, sodium antimonate, zinc borate, phosphorus-containing compounds, or halogenated compounds form useful flame retardant compositions. These compounds in combination with polymers delineated in Examples 8, 10 and 11 similarly form flame retardant compositions, combinations with the components in Example 9 form suitable flame retardant coating compositions.

While the invention has been illustrated and described in detail in the foregoing description, the same is to be construed as illustrative and not restrictive in character, it being understood that only the preferred embodiment has been shown and described and that all changes and modifications that come within the spirit of the invention are desired to be protected.

What is claimed is:

1. An oligomeric flame retardant comprising a compound of the formula:

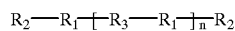

wherein n is from 1 to 11;

$R_1$ is a branched or linear alkylene group;

$R_2$ is an aryl group having an average of from about 2 to about 5 ring-substituted bromine atoms per aromatic ring; and $R_3$ is an aryl group having an average of from about 2 to about 4 ring-substituted bromine atoms per aromatic ring, wherein $R_2$ and $R_3$ are comprised of aryl groups other than a single 6 carbon aromatic ring and are further monosubstituted, disubstituted or multi-substituted with a linear or branched alkyl group.

2. A flame retardant composition comprising a flame retardant aid and a compound of the formula:

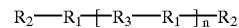

wherein n is from 1 to 11;

$R_1$ is a branched or linear alkylene group;

$R_2$ is an aryl group having an average of from about 2 to about 5 ring-substituted bromine atoms per aromatic ring; and $R_3$ is an aryl group having an average of from about 2 to about 4 ring-substituted bromine atoms per aromatic ring, wherein $R_2$ and $R_3$ are comprised of aryl groups other than a single 6 carbon aromatic ring and are further monosubstituted, disubstituted or multi-substituted with a linear or branched alkyl group.

3. A polymeric composition comprising a polymer and a flame retardant comprising a compound of the formula:

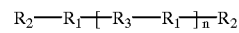

wherein n is from 1 to 11;

$R_1$ is a branched or linear alkylene group;

$R_2$ is an aryl group having an average of from about 2 to about 5 ring-substituted bromine atoms per aromatic ring; and $R_3$ is an aryl group having an average of from about 2 to about 4 ring-substituted bromine atoms per aromatic ring, wherein $R_2$ and $R_3$ are comprised of aryl groups other than a single 6 carbon aromatic ring and are further monosubstituted, disubstituted or multi-substituted with a linear or branched alkyl group.

4. A polymeric composition comprising a thermoset resin and a flame retardant comprising a compound of the formula:

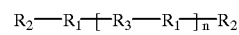

wherein n is from 1 to 11;

$R_1$ is a branched or linear alkylene group;

$R_2$ is an aryl group having an average of from about 2 to about 5 ring-substituted bromine atoms per aromatic ring; and $R_3$ is an aryl group having an average of from about 2 to about 4 ring-substituted bromine atoms per aromatic ring.

5. A method of fireproofing a material, said method comprising the step of contacting said material with a flame retardant comprising a compound of the formula:

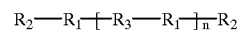

wherein n is from 1 to 11;

$R_1$ is a branched or linear alkylene group;

$R_2$ is an aryl group having an average of from about 2 to about 5 ring-substituted bromine atoms per aromatic ring; and

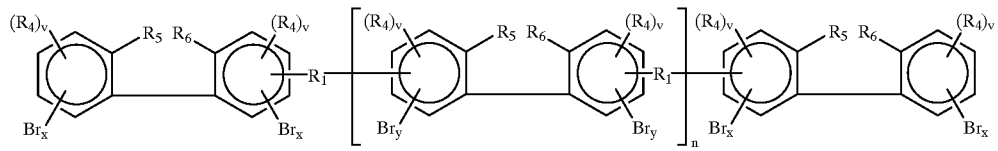

$R_3$ is an aryl group having an average of from about 2 to about 4 ring-substituted bromine atoms per aromatic ring, wherein $R_2$ and $R_3$ are comprised of aryl groups other than a single six carbon aromatic ring and are further monosubstituted, disubstituted or multi-substituted with a linear or branched alkyl group.

6. An oligomeric flame retardant comprising a compound of the formula:

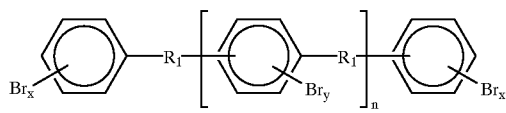

wherein
n is from 1 to 11;
$R_1$ is a linear or branched alkylene group;
x is from 4 to 5; and
y is from 2 to 4.

7. An oligomeric flame retardant comprising a compound of the formula:

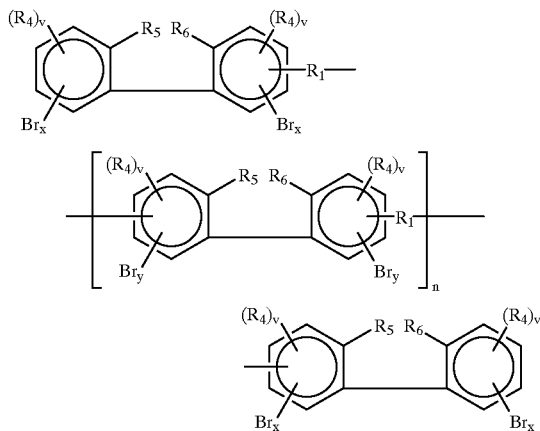

wherein
n is from 1 to 11;
$R_1$ is a linear or branched alkylene group;
$R_4$ is a linear or branched alkyl group;
$R_5$ and $R_6$ are independently an H, Br, or join to form a methylene group;
x is from 2 to 4;
y is from 1 to 3; and
v=0 or 1.

8. The flame retardant of claim 7, wherein $R_1$ contains from 1 to 6 carbon atoms.

9. A flame retardant composition comprising a flame retardant aid and a compound of the formula:

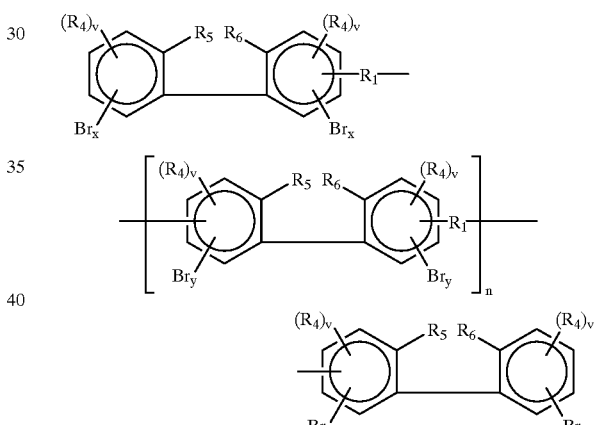

wherein
n is from 1 to 11;
$R_1$ is a linear or branched alkylene group;
$R_4$ is a linear or branched alkyl group;
$R_5$ and $R_6$ are independently an H, Br, or join to form a methylene group;
x is from 2 to 4;
y is from 1 to 3; and
v=0 or 1.

10. A polymeric composition comprising a polymer and a flame retardant comprising a compound of the formula:

wherein
n is from 1 to 11;
$R_1$ is a linear or branched alkylene group;
$R_4$ is a linear or branched alkyl group;
$R_5$ and $R_6$ are independently an H, Br, or join to form a methylene group;
x is from 2 to 4;
y is from 1 to 3; and
v=0 or 1.

11. The polymeric composition of claim 10, wherein said polymer is a thermoplastic resin.

12. The polymeric composition of claim 10, wherein said polymer is a thermoset resin.

13. The polymeric composition of claim 10, said composition further comprising a flame retardant aid.

14. A method of fireproofing a material, said method comprising the step of contacting said material with a flame retardant comprising a compound of the formula:

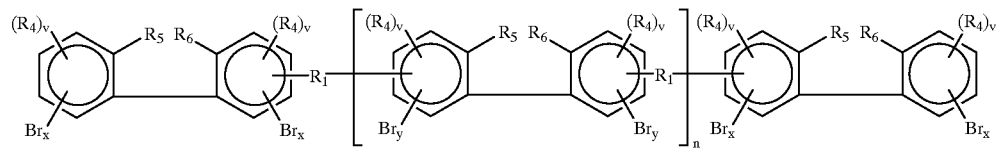
wherein
n is from 1 to 11;
$R_1$ is a linear or branched alkylene group;
$R_4$ is a linear or branched alkyl group;
$R_5$ and $R_6$ are independently an H, Br, or join to form a methylene group;
x is from 2 to 4;
y is from 1 to 3; and
v=0 or 1.
15. The method of claim 14, said flame retardant further comprising a flame retardant aid.
* * * * *